(12) United States Patent
Portoghese et al.

(10) Patent No.: US 8,609,682 B2
(45) Date of Patent: Dec. 17, 2013

(54) ANALGESIC AGENTS

(75) Inventors: Philip S. Portoghese, St. Paul, MN (US); Ajay S. Yekkirala, St. Paul, MN (US)

(73) Assignee: Regents of The University of Minnesota, St. Paul, MN (US)

( * ) Notice: Subject to any disclaimer, the term of this patent is extended or adjusted under 35 U.S.C. 154(b) by 84 days.

(21) Appl. No.: 13/003,691

(22) PCT Filed: Jul. 10, 2009

(86) PCT No.: PCT/US2009/050303
§ 371 (c)(1),
(2), (4) Date: Jun. 24, 2011

(87) PCT Pub. No.: WO2010/006299
PCT Pub. Date: Jan. 14, 2010

(65) Prior Publication Data
US 2011/0251227 A1    Oct. 13, 2011

Related U.S. Application Data

(60) Provisional application No. 61/080,128, filed on Jul. 11, 2008.

(51) Int. Cl.
*A61K 31/485* (2006.01)
*C07D 489/08* (2006.01)

(52) U.S. Cl.
USPC .......................................... 514/282; 546/44

(58) Field of Classification Search
USPC ............................................ 514/282; 546/44
See application file for complete search history.

(56) References Cited

U.S. PATENT DOCUMENTS

| 6,177,438 B1 | 1/2001 | Nagase et al. |
| 6,277,859 B1 | 8/2001 | Nagase et al. |

FOREIGN PATENT DOCUMENTS

| EP | 0661283 | 10/1998 |
| EP | 0663401 | 6/2000 |
| WO | WO 2005/117589 A1 | 12/2005 |

OTHER PUBLICATIONS

Kawai et al., Design, synthesis, and structure-activity relationship of novel opioid κ-agonists, *Bioorganic & Medicinal Chemistry* 16, pp. 9188-9201, 2008.
Le Naour, et al., "Opioid Activity of Spinally Selective Analogues of *N*-Naphthoyl-βnaltrexamine in HJEK-293 Cells and Mice", *Journal of Medicinal Chemistry*, pp. A-H, 2011.
Li et al., "Design, Synthesis, and Biological Evaluation of 6α- and 6β-*N*-Heterocyclic Substituted Naltrexamine Derivatives as μ Opioid Receptor Selective Antagonists", *J. Med. Chem.*, 52, pp. 1416-1427, 2009.
McCurdy et al., "Naphthalene Dicarboxaldehyde as an Electrophilic Fluorogenic Moeity for Affinity Labeling: Application to Opioid Receptor Affinity Labels with Greatly Improved Fluorogenic Properties", *Journal of Medical Chemistry*, vol. 45, No. 14, pp. 2887-2890, 2002.
Patent Cooperation Treat, International Searching Authority, Search Report and Written Opinion for PCT/US2009/050303, 19 pages, dated Nov. 23, 2009.
Zhang et al., "Specific Cross-Linking of Lys233 and Cys235 in the Mu Opioid Receptor by a Reporter Affinity Label", *Biochemistry*, 44, pp. 2271-2275, 2005.

*Primary Examiner* — Charanjit Aulakh
(74) *Attorney, Agent, or Firm* — Viksnins Harris & Padys PLLP

(57) ABSTRACT

The invention provides a compound of formula (I) or a salt thereof, as well as compositions comprising such compounds. The compounds and compositions are useful as analgesics.

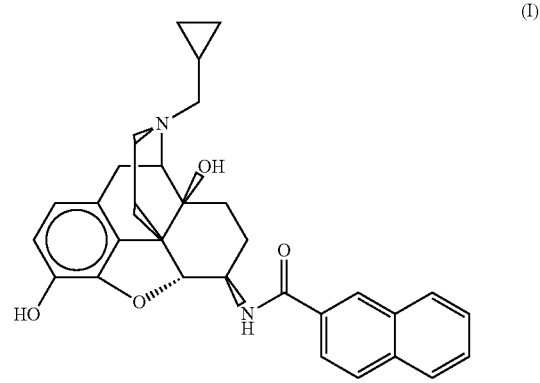

(I)

8 Claims, 7 Drawing Sheets

ANALGESIC AGENTS

CROSS-REFERENCE TO RELATED APPLICATION(S)

This patent application claims the benefit of priority of U.S. application Ser. No. 61/080,128, filed Jul. 11, 2008, which application is herein incorporated by reference.

GOVERNMENT FUNDING

The invention described herein was made with Government support under Grant Number DA01533 awarded by NIDA. The United States Government has certain rights in the invention.

BACKGROUND OF THE INVENTION

Pain represents a major health and economic problem throughout the world. Despite advances in understanding the physiological basis of pain, an ideal analgesic has yet to be discovered.

Among analgesic drugs, the opioid class of compounds is widely used for pain treatment. The opioid drugs produce effects by interacting with the opioid receptors. The existence of at least three opioid receptor types, μ (mu), δ (delta), and κ (kappa) has been established. All three opioid receptor types are located in the human central nervous system, and each has a role in the mediation of pain. Opioid receptors are also known to undergo heterodimerization when coexpressed in cultured cells. Among the reported opioid receptor heterodimers are delta/kappa, delta/mu, and kappa/mu. In cultured cells the effect of heterodimerization may be manifested in a number of ways, including changes in efficacy, function, trafficking, and ligand recognition.

Morphine and related opioids currently used as analgesics produce their analgesia primarily through their agonist action at mu opioid receptors. The administration of these drugs is limited by significant side effects such as the development of tolerance, physical dependence, addiction liability, constipation, respiratory depression, muscle rigidity, and emesis. Accordingly, there is a need for improved analgesics. In particular, there is a need for analgesics that are more potent than morphine or that produce fewer or reduced side-effects compared to existing analgesics.

SUMMARY OF THE INVENTION

Applicant has discovered a compound of formula (I) that selectively activates kappa/mu opioid receptor heterodimers in HEK-293 cells and that induces potent analgesia in mice. Accordingly, in one embodiment, the invention provides a compound of formula (I):

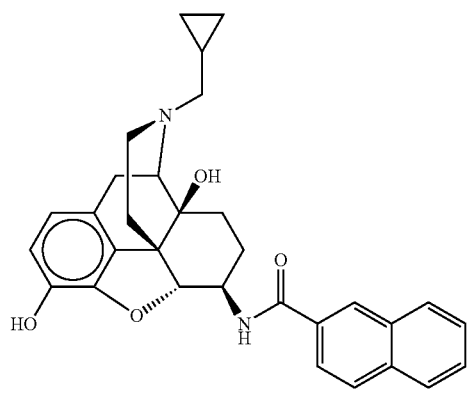

(I)

or a pharmaceutically acceptable salt thereof for use in medical therapy.

In another embodiment, the invention provides a use of a compound of formula (I), or a pharmaceutically acceptable salt thereof, to prepare a medicament for producing analgesia in an animal (e.g. human).

In another embodiment, the invention provides a use of a compound of formula (I), or a pharmaceutically acceptable salt thereof, to prepare a medicament for producing analgesia in an animal (e.g. human) wherein the analgesia is produced while causing less inhibition of GI transit than is caused by administration of a similar effective dosage of morphine to the animal (e.g. human).

In another embodiment, the invention provides a use of a compound of formula (I), or a pharmaceutically acceptable salt thereof, to prepare a medicament for producing analgesia in an animal (e.g. human) wherein the analgesia is produced while causing less dependence than is caused by administration of a similar effective dosage of morphine to the animal (e.g. human).

In another embodiment, the invention provides a use of a compound of formula (I), or a pharmaceutically acceptable salt thereof, to prepare a medicament for producing analgesia in an animal (e.g. human) wherein the analgesia is produced while causing less tolerance than is caused by administration of a similar effective dosage of morphine to the animal (e.g. human).

In another embodiment, the invention provides a compound of formula (I), or a pharmaceutically acceptable salt thereof for the prophylactic or therapeutic treatment of pain.

In another embodiment, the invention provides a use of a compound of formula (I), or a pharmaceutically acceptable salt thereof, for the prophylactic or therapeutic treatment of pain, wherein the treatment causes less inhibition of GI transit than is caused by administration of a similar effective dosage of morphine to the animal.

In another embodiment, the invention provides a use of a compound of formula (I), or a pharmaceutically acceptable salt thereof, for the prophylactic or therapeutic treatment of pain, wherein the treatment causes less dependence than is caused by administration of a similar effective dosage of morphine to the animal.

In another embodiment, the invention provides a use of a compound of formula (I), or a pharmaceutically acceptable salt thereof, for the prophylactic or therapeutic treatment of pain, wherein the treatment causes less tolerance than is caused by administration of a similar effective dosage of morphine to the animal.

In another embodiment, the invention provides a compound of formula (I), or a salt thereof.

In another embodiment, the invention provides a pharmaceutical composition comprising a compound of formula (I), or a pharmaceutically acceptable salt thereof; and a pharmaceutically acceptable diluent or carrier.

In another embodiment, the invention provides a method for producing analgesia in an animal comprising administering a compound of formula (I), or a pharmaceutically acceptable salt thereof, to the animal (e.g. human).

In another embodiment, the invention provides a method for producing analgesia in an animal, comprising administering to the animal an amount of a compound of formula (I), or a pharmaceutically acceptable salt thereof, that is effective to produce analgesia while causing less inhibition of GI transit than is caused by administration of a similar effective dosage of morphine to the animal (e.g. human).

In another embodiment, the invention provides a method for producing analgesia in an animal, comprising administering to the animal an amount of a compound of formula (I), or a pharmaceutically acceptable salt thereof, that is effective to produce analgesia while causing less dependence than is caused by administration of a similar effective dosage of morphine to the animal (e.g. human).

In another embodiment, the invention provides a method for producing analgesia in an animal, comprising administering to the animal an amount of a compound of formula (I), or a pharmaceutically acceptable salt thereof, that is effective to produce analgesia while causing less tolerance than is caused by administration of a similar effective dosage of morphine to the animal (e.g. human).

In another embodiment, the invention provides processes and intermediated disclosed herein that are useful for preparing a compounds of formula (I) or a salt thereof.

DETAILED DESCRIPTION

Figure 1:
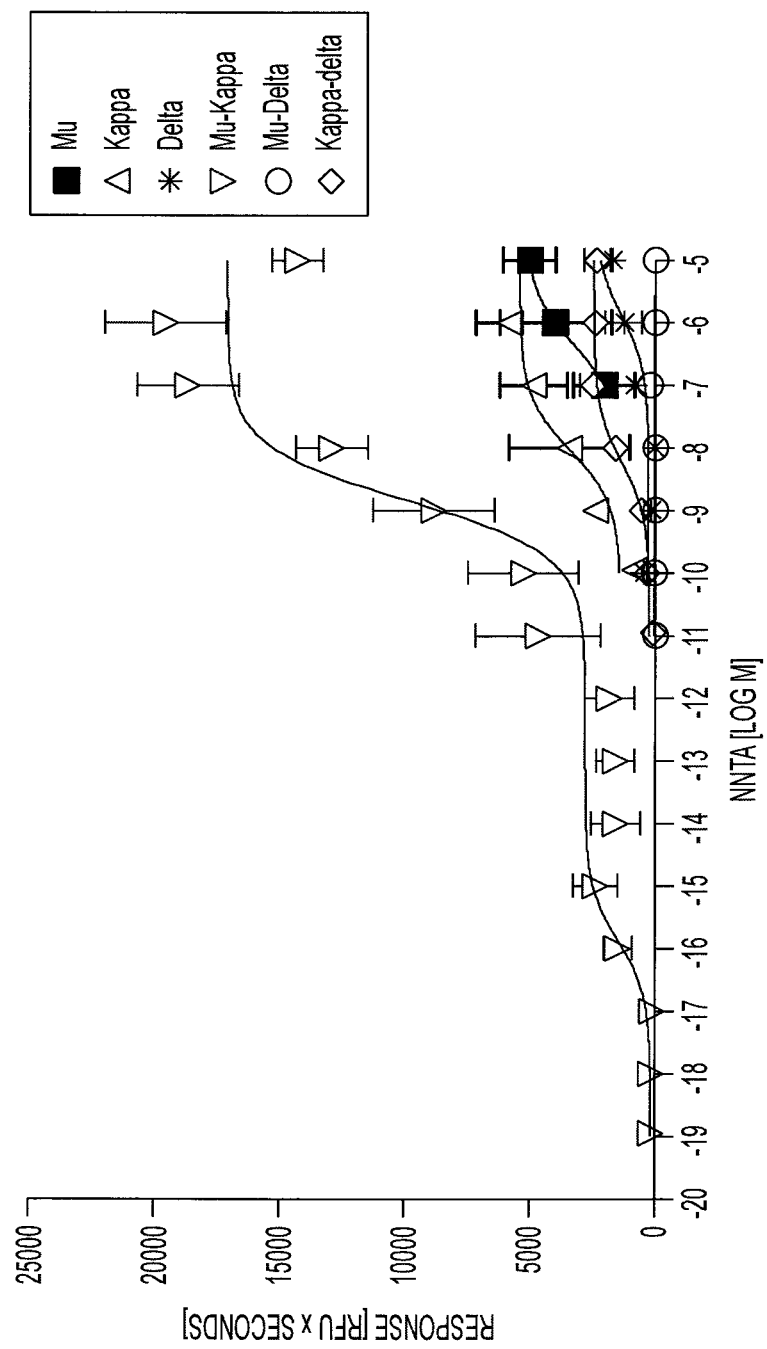
FIG. 1. Concentration response curves from calcium release experiments, which were performed in HEK-293 cells coexpressing mu/kappa heterodimers.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form, by recrystallization techniques, by synthesis from optically-active starting materials, by chiral synthesis, or by chromatographic separation using a chiral stationary phase).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The analgesic and pharmacological properties of a compound can be determined using models that are well known to the art or by Test A. Additionally, a compound may be used as a pharmacological tool for investigation of mu/kappa receptor function by performing the studies detailed in this test or by further studies well known in the art.

Test A: Receptor Binding and Activation Studies

In cell culture, competition binding, $Ca^{2+}$ release assays or [$^{35}$S]GTPγS assays can be used to assess the affinity of a compound for the different opioid receptors.

Cell Culture and Transfections cDNAs encoding murine kappa, delta and mu opioid receptors are inserted separately into the mammalian expression vector pcDNA3 (Invitrogen, Carlsbad, Calif.) and these are then used to generate the singly expressing stable HEK-293 cell lines. HEK-293 cells stably co-expressing mu-kappa, kappa-delta and mu-delta receptors are generated as previously described (Waldhoer, M., et al. (2005) Proc. Natl. Acad. Sci. 102, 9050-9055). HEK-293 cells are cultured at 37° C. in Dulbelcco's modified Eagle's medium supplemented with 10% fetal bovine serum and P/S antibiotics. For cells singly expressing opioid receptors, G418 is used as the selection antibiotic; G418 and Zeocin are used for selecting for cells co-expressing two opioid receptors. The intracellular calcium release experiments are performed with the stable cell lines, in which a chimeric G-protein $\Delta 6$-$G_{\alpha qi4-myr}$ (Kostenis, E. (2001) Trends Pharmacol. Sci. 22, 560-564) (200 ng/20,000 cells) is transiently transfected using OptiMEM medium (Invitrogen), Lipofectamine 2000 (Invitrogen, Carlsbad Calif.) and the manufacturer's protocol.

Competition Binding

The experiments are performed using HEK 293 cells genetically modified to produce wild-type μ, κ, or δ opiate receptors and co-expressing mu/kappa opioid receptors. Ten concentrations of the tested compounds (50 μL) are added to test tubes, which contain 0.5 nM [$^3$H]diprenorphine ($\approx 1.0\times$ $K_D$)(50 μL) or selective radioligands, [$^3$H]DAMGO and [$^3$H] U69593 (both 2.0 nM), and whole cells (75 mm$^2$ plate, 80-90% confluent) suspended in 12 ml HEPES buffer (25 mM, pH=7.4) (400 μL) (final volume of 500 μl). Non-specific binding is measured using 10 μM naloxone. Assays are incubated at room temperature for 90 min. and then filtered using a Brandel M-48 tissue harvester through Whatman GF/C filter paper that is pre-soaked in 0.25% poly(ethyleniminie). Filters are washed three times with ice cold HEPES buffer and radioactivity is counted using a LS 6500 liquid scintillation counter (Beckman, Fullerton, Calif.). All measurements are performed in triplicate. IC$_{50}$ values are calculated using PRISM software (GraphPad, San Diego, Calif.) utilizing non-linear regression of the data normalized to fit a sigmoidal dose-response curve with a variable slope (100% defined at concentration=0 (total binding) and 0% defined at the value of non-specific binding). $K_i$ values are determined from the Cheng-Prusoff equation assuming a single site binding model. Values reported are mean $K_i$±standard error of the mean (SEM) of three or more independent experiments (Oliver, H. et al. (1951) J. Biol. Chem. 193, 265-275; Werling, L. L. et al. (1985) J. Pharmacol. Exp. Ther. 233, 722-728).

Compound of formula (I) was examined using this test and the results are detailed below. In the competition binding assay using [$^3$H]diprenorphine and cells singly expressing the opioid receptors, NNTA was found to bind with high affinity to mu ($K_i$=0.077 pM) and kappa ($K_i$=0.084 pM). NNTA possessed much lower binding affinity for the delta opioid receptor ($K_i$=1.39 nM). The affinity of NNTA for mu/kappa receptor heterodimers was also examined using the selective radioligands [$^3$H]DAMGO (mu) and [$^3$H]U69593 (kappa) and cells expressing single mu or kappa receptors or co-expressing the two receptors. Competition binding with these radioligands afforded $K_i$ values that were essentially identical between the cells co-expressing mu/kappa receptors and cells singly expressing mu or kappa receptors (Table 1).

TABLE 1

Competition binding of selective radioligands and NNTA in HEK-293 cells co-expressing mu/kappa receptors or individually expressing mu and kappa receptors.

| | Radioligands | |
|---|---|---|
| Cell Type | [$^3$H]DAMGO(μ) Ki (pM) | [$^3$H]U69593(κ) Ki (pM) |
| μ/κ coexpressed | 2.07 ± 1.18 | 3.39 ± 0.38 |
| μ | 1.25 ± 0.176 | — |
| κ | — | 9.47 ± 5.75 |

Data shown as Mean ± SEM (n = 3).

$Ca^{2+}$ Release Experiments

Calcium mobilization studies are performed using six different cell lines, which stably express the opioid receptors either singly (mu, kappa or delta) or in pairs (mu/kappa, kappa/delta or mu/delta). Prior to the experiment, co-immunoprecipitation are performed on the lines expressing pairs of receptors to confirm the expressed receptors are heterodimeric (Waldhoer, M. et al. (2005) Proc. Natl. Acad. Sci. 102, 9050-9055). To couple the Gi/Go opioid receptors to the calcium releasing mechanism, a chimeric Gα-protein (Δ6-$G_{qi4-myr}$) is transiently transfected into the cells using Lipofectamine 2000 (200 ng/20,000 cells) (Invitrogen, Carlsbad Calif.) and OptiMEM medium. The following day 20,000 cells/well are seeded into 96-well black plates (Corning Inc.). The FLIPR calcium kit (Molecular Devices), which contains a dye that fluoresces in response to receptor activation and $Ca^{2+}$ ion chelation, is used for the assay. On the 3$^{rd}$ day (i.e., 48 hours after transfection), the cells are incubated with the dye for one hour. After addition of the opioid ligand, which is used in varying concentrations, the plates are assayed in a Flexstation-III apparatus (Molecular Devices). The response is measured as Relative Fluorescence Units (RFUs) and the time of the response is measured in seconds. A response window of 33 seconds after ligand addition is used to measure the response before calcium ion reuptake mechanisms cause a drop in fluorescence. Area under the curve (RFU×seconds) is computed for each concentration, which is then plotted as a concentration response curve using non-linear regression. The different cell lines are evaluated for consistent receptor expression and activation using standard ligands DAMGO (mu), U69593 (kappa) and DPDPE (delta) as controls. To account for well-well variability, 4 well replications are performed for each concentration of the ligand. Importantly, each ligand is tested in at least 3 independent replications where each replicate experiment consists of cells transiently transfected with the chimeric G-protein on a separate day, thus ensuring true biological replication. The representative curves, $EC_{50}$ and $AUC_{peak}$ values are all a cumulative of data from the 4 internal/dependent and 3 independent replications. Thus any variability due to transfection is contained within the error bars and has been taken into account.

The $Ca^{2+}$ release experiment was performed using the compound of formula (I) and it was shown that NNTA selectively activates mu/kappa opioid receptor heterodimers. NNTA was most efficacious in the cells co-expressing mu/kappa opioid receptors ($A_{peak}$=15974 RFU-Seconds) compared with cells expressing the rest of the opioid receptors (FIG. 1, Table 2). Interestingly, the concentration response curve of NNTA at the mu/kappa opioid receptor was biphasic with activation observed at concentrations as low as $10^{-16}$ M (FIG. 1). Thus, NNTA was not only most active but also most potent at the mu/kappa opioid receptor heterodimers (Table 2). Specifically, in kappa/mu co-expressing cells the potency ($EC_{50}$=0.70 nM) of NNTA was 1000-fold greater compared to cells that contained singly expressed mu, and 100-fold greater in cells expressing kappa receptors. There was no observable activation in delta or mu/delta cell lines. The binding of NNTA to kappa/mu cells (Ki=3.4 pM) was similar to that of individually expressed kappa and mu receptors, but substantially greater than delta (Table 1). These data suggest that the enhanced activation mediated by the kappa/mu heterodimer is not due to any affinity difference.

TABLE 2

(a) $EC_{50}$ and (b) $^a$AUC$_{peak}$ values for $Ca^{2+}$ release from HEK-293 cells stably expressing opioid receptors.

| Cells | NNTA | DAMGO | U69593 | DPDPE |
|---|---|---|---|---|
| (a) $EC_{50}$ (nM)$^c$ | | | | |
| Mu/kappa** | I: 1.3E−07 ± 1.1E−07 II: 0.70 ± 0.33 | 13.4 ± 10.8 | 6.5 ± 4.1 | — |
| Kappa/delta | 17.9 ± 10.6 | — | 2.8 ± 1.3 | 21.0 ± 20.4 |
| Mu/delta | >1000 | 1.5 ± 1.4 | — | 17.6 ± 15.9 |
| Mu | >1000 | 10.6 ± 0.4 | — | — |
| Kappa | 51.4 ± 11.0 | — | 33.7 ± 22.1 | — |
| Delta | >1000 | — | — | 11.0 ± 10.5 |
| (b) $^a$AUC$_{peak}$ (RFU$^b$ × seconds)$^c$ | | | | |
| Mu/kappa | 15947 ± 1087 | 5562 ± 668 | 4899 ± 566 | |
| Kappa/delta | 2462 ± 197 | | 11803 ± 1291 | 10153 ± 1479 |

TABLE 2-continued (a) $EC_{50}$ and (b) $^{a}AUC_{peak}$ values for $Ca^{2+}$ release from HEK-293 cells stably expressing opioid receptors.

| Cells | NNTA | DAMGO | U69593 | DPDPE |
|---|---|---|---|---|
| Mu/delta | 57 ± 42 | 12054 ± 1281 | — | 10504 ± 969 |
| Mu | 5203 ± 1622 | 9989 ± 702 | — | — |
| Kappa | 5548 ± 1285 | — | 6452 ± 737 | — |
| Delta | 2441 ± 409 | — | — | 8319 ± 1117 |

**There are two EC50 values for mu/kappa due to the biphasic concentration curve
[a]AUC = Area Under the Curve (RFU[b] x seconds)
[b]RFU = Relative Fluorescent Units
[c]Values presented as Mean ± SEM (n = 12-16)

[$^{35}$S]GTPγS Assay

The assay is performed as described previously (Mullaney, I (1999) In Signal Transduction: A practical approach, 2nd ed., Oxford University Press, 100-101). Briefly, varying concentrations of ligand, HEK-293 cell membranes expressing opioid receptors and [$^{35}$S]GTPγS (Perkin-Elmer) are combined together in membrane buffer (50 mM Tris-HCl, 3 mM $MgCl_2$, 0.2 mM EGTA, 100 mM NaCl and 0.5% BSA). This mixture is incubated at 37° C. in a 96 well plate for one hour and then filtered onto a filter plate (Multiscreen HTS, Millipore) and counted for [$^{35}$S]. At least 3 replications are performed for each treatment. It is important to note that the [$^{35}$S]GTPγS binding to endogenous Gα proteins is being measured and no chimeric G-protein is added to the cells for these experiments. Thus, the data observed is independent of the calcium release experiments.

Figure 2:
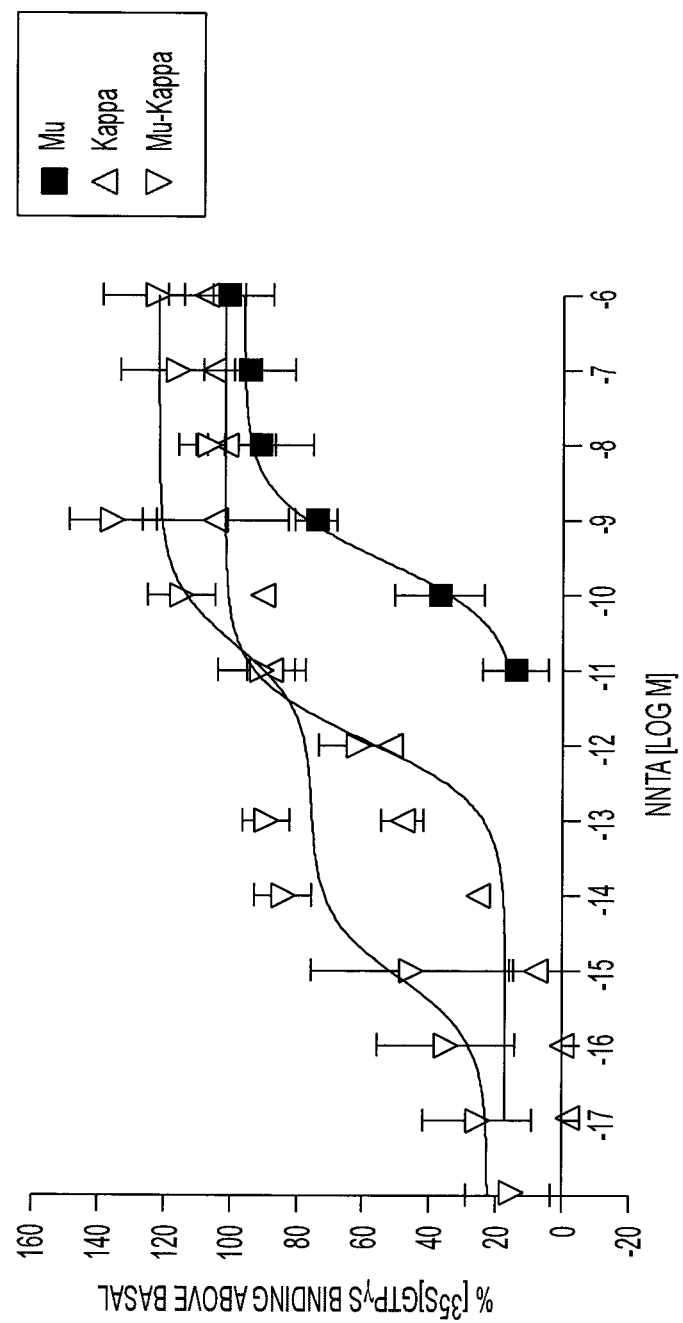
FIG. 2. Concentration response curves from [$^{35}$S]GTPγS experiments, which were performed in HEK-293 cells coexpressing mu/kappa heterodimers.

To confirm the results from the $Ca^{2+}$ release experiments, the compound of formula (I) was evaluated using the [$^{35}$S] GTPγS assay in membranes isolated from HEK 293 cells stably expressing mu, kappa and mu/kappa opioid receptors. NNTA was again most potent at the mu/kappa opioid heterodimers ($EC_{50}1$=0.81 femM; $EC_{50}2$=22 picoM) when compared with kappa (1.1 picoM) and mu (0.3 nM). This time the biphasic concentration response was even more pronounced with greater activation in the sub-picoM range (FIG. 2).

The equal binding affinity of NNTA for mu and kappa receptors may be relevant to the observed biphasic activation of mu-kappa heteromers. Several possible scenarios could account for such a profile. One possibility is that activation triggered by binding of NNTA to either the mu or kappa recognition site, gives rise to two singly occupied populations of mu-kappa heteromers that are differentially activated. Another possibility involves a mixture of doubly and singly occupied mu-kappa heterodimers.

The analgesic properties of a compound can be determined using models that are well known to the art or by Test B described below, which uses guinea pig ileum (GPI) and the mouse tail flick procedure.

Test B: Analgesic Testing

Guinea Pig Ileum (GPI) Assay

Longitudinal muscle strips of the guinea pig ileum (Charles River laboratory, Wilmington, Mass.) are prepared for the experiments using the method described by H. P. Rang ((1964) Br. J. Pharmac. Chemother. 22, 356-365). The assays are subsequently conducted as previously described (Portoghese, P. S. and Takemori, A. E. (1985) Life Sci. 36, 801-805).

Tail Flick Experiment

Animal Housing. Male ICR-CD1 mice (18-25 g or 30-35 g; Harlan Labs, Madison, Wis.), are used throughout the testing, except male ICR mice weighing 25-35 gm (Harlan Sprague Dawley) are used in the i.v. and chronic i.c.v. studies. The mice are housed in groups of 8 in a temperature/humidity controlled environment with unlimited access to food and water and maintained on a 12 hour light/dark cycle.

Acute Drug Administration. For acute drug administration, all solutions are dissolved in distilled water and administered in conscious mice. For i.t. and i.c.v, all drugs are administered in a 5-µl volume according to the method previously described by Hylden, J. L. K. and Wilcox, G. L. ((1980) Eur. J. Pharmacol. 67, 313-316) for i.t. and as described by Haley, T. J. and McCormick, W. G. ((1957) Br. J. Pharmac. 12, 12-15) for the i.c.v. injections.

Tail Flick Procedure. Antinociception is evaluated by the modified radiant heat tail flick assay (Tulunay, F. C. and Takemori, A. E. (1974) J. Pharmacol. Exp. Ther. 190, 395-400). Briefly, a radiant heat source is applied to the dorsal side of the tail, and the latency to flick away from the heat source is recorded. Each animal serves as its own control. Mice are tested once before injection (control time). After injection or oral administration, the mice are tested at the time of peak drug response (drug time), as determined by pilot time course studies. For example, the peak time for NNTA i.t. is 5 minutes, the peak time for NNTA i.c.v is 10 minutes and the peak time for NNTA oral is 60 minutes. The data is made quantal by designating a positive antinociceptive response of an animal as those that increased their latency to tail flick (after drug treatment) by at least three standard deviations above the mean of the baseline latency of the whole group (Tallarida, 2000). The light source is manually turned off if the mouse does not flick its tail after the three standard deviation criteria for a positive response. The light intensity is adjusted so that control times are between 1.5 and 2.5 s. At least three groups of 8-10 mice are used for each drug paradigm, and each mouse is used only once.

Percent maximum possible effect (% MPE) is calculated as follows:

$$\frac{\text{Drug Time (s)} - \text{Control Time (s)}}{10\text{ s} - \text{Control Time (s)}} \times 100\% = \% \text{ MPE}$$

Graded dose response curves of at least 4 doses with at least 8 mice per dose are generated from the % MPE data. $ED_{50}$ values and 95% confidence intervals are calculated by using the parallel line assay (Finney, D. J. (1964) Statistical Methods in Biological Assay, 2nd ed., Hafner, New York). When $ED_{50}$ values are compared, all the data are analyzed together and values were considered significantly different if they do not lie in each other's 95% confidence limits at $p<0.05$.

For the i.v. and chronic i.c.v. studies, the assay is performed as described above with minor variations. Specifically, the mice are tested using the radiant heat tail flick test adjusted to give a 2-3 sec baseline latency time with a maximum 10 sec cut-off time. For these experiments, baseline latency times are determined, drugs are injected either i.v. or i.c.v. and tail flick latency times are again determined at the time of peak antinociceptive response as determined from preliminary studies. The time of peak antinociception are as follows: morphine i.v. is 15 min, i.v. NNTA is 20 min, and i.c.v. NNTA is 10 min. $ED_{50}$ values (95% confidence intervals) are calculated using the Prism software (Daniels, D. J. et al. (2005) Proc. Natl. Acad. Sci. 102, 19208-19213).

Figure 3:
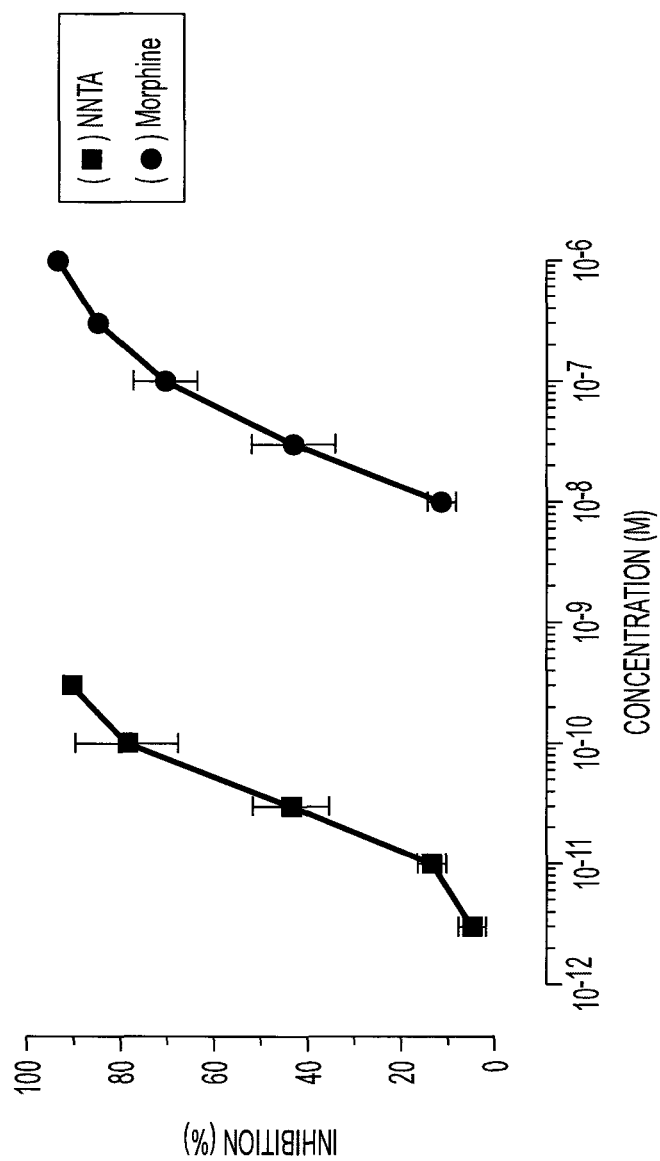
FIG. 3. NNTA and morphine inhibition (%) measured in the Hartley guinea pig ileum.
Figure 4:
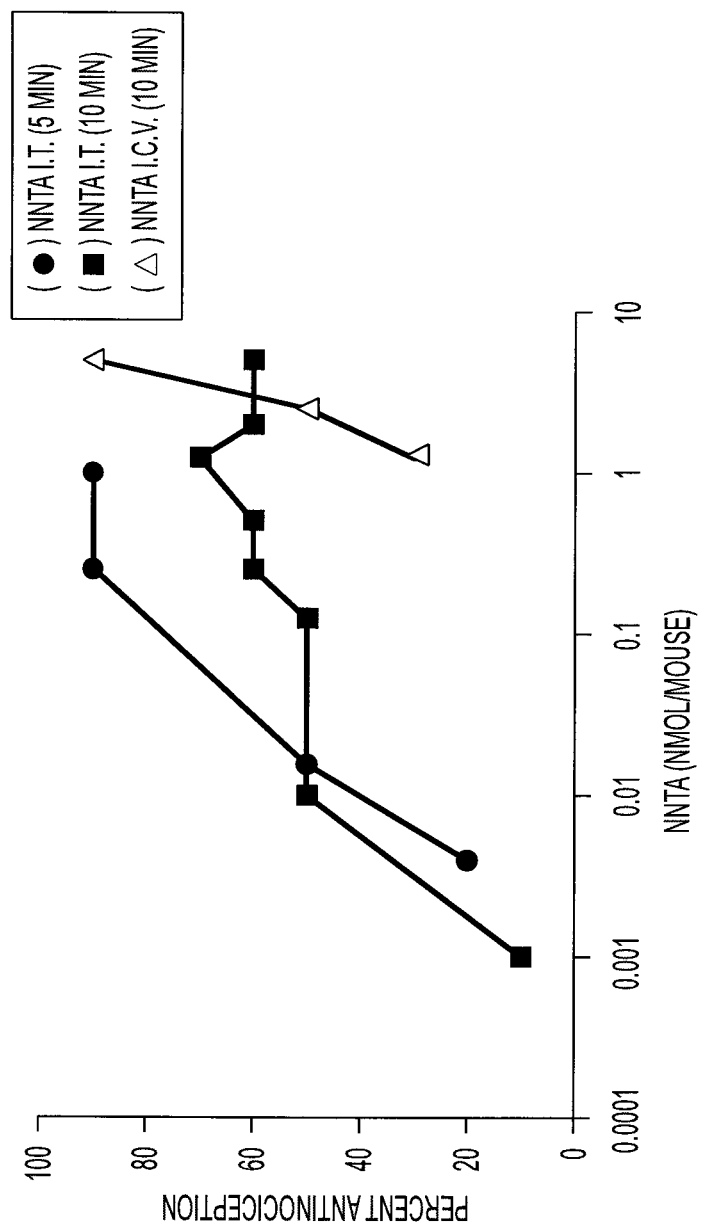
FIG. 4. Antinociception measured 5 and 10 min after intrathecal (i.t.) administration of NNTA and 10 min after intracerebroventricular (i.c.v.) administration of NNTA.

The GPI assay and the Tail Flick procedure were performed using the compound of formula (I) and it was shown that NNTA is a potent analgesic in vivo. In the GPI assay, NNTA was found to be 1225 times more potent than morphine ($IC_{50}$=0.038 nM v. $IC_{50}$=50.6 nM, respectively) (FIG. 3). NNTA also produced potent antinociception through both intrathecal (i.t.) and intracerebroventricular (i.c.v.) routes when tested using the tail-flick procedure (FIG. 4). A peak time of 10 min was used for the i.t. and i.c.v. administration of NNTA. A full i.t. dose response was observed after 5 min and at 10 min NNTA behaved like a partial agonist. The antinociceptive $ED_{50}$ (95% CI) values were 18.7 (10.3-32.8) pmol/mouse for the i.t. route and 2.06 (1.09-3.27) nmol/mouse for the i.c.v. injections. Thus, NNTA was 110-fold more potent when administered spinally than when given supraspinally. This large difference raised the possibility that NNTA might be activating phenotypic opioid receptors that are more responsive in the cord when compared to those in the brain (FIG. 4).

Figure 5:
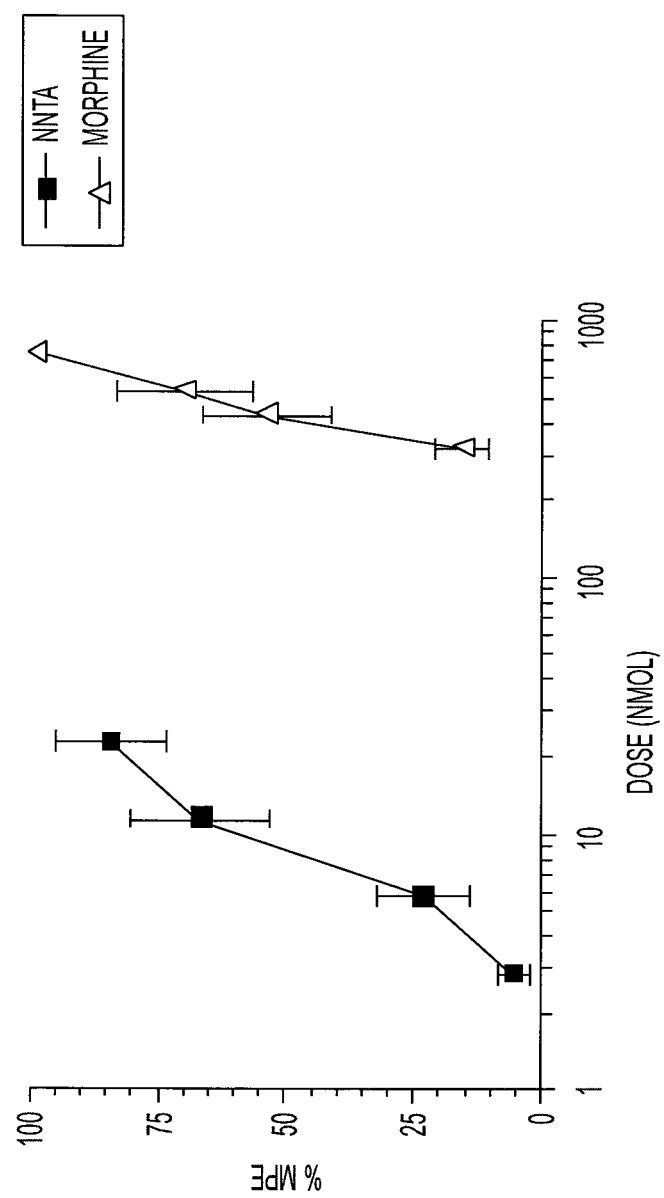
FIG. 5. Graded dose response curves for i.v. administered NNTA and morphine. Percent maximum possible effect (% MPE) calculated from mouse tail flick data.

NNTA was also found to be a potent antinociceptive agonist when administered by i.v. (FIG. 5). The $ED_{50}$ value for i.v. was 8.8 (6.8-11.5) nmol, whereas the i.v. morphine $ED_{50}$ value was 420 (378-469) nmol. Thus, NNTA was about 50-fold more potent than morphine after systemic administration. An 80% oral dose response was observed at 60 min and the drug was inactive at 120 min. The oral $ED_{50}$ value was 2.86 mg/kg (1.74-4.29).

The control animals received only distilled water and showed no antinociception in these studies.

Selective antagonists can be used to pharmacologically characterize the receptors that are activated by a compound of interest. This characterization can be performed using models that are well known to the art or by Test C, which uses guinea pig ileum (GPI) and the mouse tail flick procedure in conjunction with specific antagonists.

Test C: Pharmacological Characterization of Activated Receptors

The GPI assay and the mouse tail flick procedure are performed as described above in Test C. $ED_{50}$ ratios for antagonism are determined using selective antagonists for the kappa, mu, and delta opioid receptors (norbinaltorphimine (norBNI), Cys2-Tyr3-Orn5-Pen7-amide (CTOP) and naltrindole (NTI), respectively). NTI and norBNI are synthesized as described previously (Portoghese, P. S., et al. (1987) Life Sci. 13, 1287-1292; Portoghese, P. S., et al. (1988) Eur. J. Pharmacol. 146, 185-186). CTOP is obtained from the National Institute of Abuse (Gulya, L. K., et al. (1986) Life Sciences 38, 2221-2229; Pelton, J. T., et al. (1986) J. Med. Chem. 29, 2370-2375). The drugs are administered so that the antagonist and agonist effects peak simultaneously. For example, the peak time for the antagonists (CTOP, NTI and norBNI) is 20 minutes while the agonist peak times are 5 minutes for NNTA i.t. and 10 minutes for NNTA i.c.v.

Selective antagonists were used in conjunction with the GPI assay and the tail flick procedure to investigate the possible agonism mechanisms for the compound of formula (I). Neither the kappa antagonist, norBNI, nor the delta antagonist, NTI, antagonized NNTA in the GPI studies. In ICR-CD 1 mice, antagonist $ED_{50}$ ratios were elucidated for selective antagonists CTOP (mu), NTI and norBNI. Again, CTOP and NTI did not antagonize NNTA. However, norBNI seemed to be slightly antagonizing NNTA i.c.v. ($ED_{50}$ ratio=5.63) and more potently i.t. ($ED_{50}$ ratio=38.26). These data revealed that only norBNI antagonized the effect of NNTA, which suggested involvement of kappa receptors in the antinociceptive response. However, without a selective mu-kappa antagonist that would distinguish between heteromeric and homomeric receptors, it is not clear whether NNTA was mediating antinociception via mu-kappa heteromers or kappa homomeric receptors. Reports for the presence of putative delta-kappa heteromers in the spinal cord, our cell-based data that show NNTA to be substantially more efficacious in activating mu-kappa heteromers and the exceptional potency of i.t. NNTA, tend to support the concept that the observed spinal antinociception is mediated principally via mu-kappa heteromers.

The tolerance and dependence properties of a compound of the invention can be determined using pharmacological models which are well known to the art (e.g. see Daniels, D. J. et al. (2005) Proc. Natl. Acad. Sci. USA 102, 19208-19213) or they can be evaluated by Test D as described below.

Test D: Dependence and Tolerance Assays
Chronic ICV Infusion

The mice used in these experiments and their housing conditions are detailed above. Mice are infused i.c.v. with saline or the drug to be tested (i.e. NNTA 7.1 nM) for 3 days using osmotic mini pumps, as previously described (Lenard, N. R. and Roerig, S. C. (2005) Eur. J. Pharmacol. 527, 71-76). Briefly, the osmotic minipumps (model 1003D, Alzet, Durect Corporation, Cupertino, Calif.) are filled with saline or the drug of interest. The dose of each drug is twelve times the $ED_{50}$ dose (NNTA 27.6 nmol/hour). The minipumps are connected by a 1.6-1.8 cm length of PE-60 tubing to a 3-mm long cannula (osmotic pump connector cannula, Plastics One, Roanoke, Va.) and primed in sterile saline at 37° C. overnight. The next day, mice are anesthetized with Avertin (2,2,2-tribromoethanol (370 mg/kg, IP)/tert amyl alcohol (0.16 mg/kg, IP)) before surgery. The scalp is shaved and an incision is made along the midline of the scalp. Hemostats are used to make a pocket under the skin between the shoulder blades. The skull is scraped clean of periosteum so that the cannula pedestal will properly adhere to the skull. A micro drill (Fine Science Tools Inc., Foster City, Calif.) is used to drill a hole approximately 1.6 mm lateral and 0.6 mm caudal to bregma. The minipump is placed between the shoulder blades, the cannula is inserted in the drilled hole into the lateral ventricle, and the cannula pedestal is affixed to the skull with cyanoacrylate glue. The animals are allowed to recover on a heating pad (Fine Science Tools, Foster City, Calif.) and are returned to their cages in the animal facility for three days.

Withdrawal and Tolerance Assays

The development of physical dependence can be assessed by quantifying withdrawal jumping observed during precipitated withdrawal on the fourth day after surgery. Mice are injected with naloxone (1 mg/kg, sc) and placed into a 4 L glass beaker for 10 minutes. During those 10 minutes, vertical jumps are counted as withdrawal signs.

To test the degree of tolerance developed, the osmotic minipump is removed and the mice are returned to their cages for two hours. The mice are then administered an acute i.c.v. dose of NNTA. Tail flick latencies (described above) are measured and % MPE values are calculated as described above. ED50 values are considered significantly different when the 95% confidence intervals do not overlap. Significance is accepted at $p<0.05$.

Dependence Assay

Conditioned place preference (CPP) is a technique used to measure the rewarding properties of a drug. Two sides of the CPP apparatus have both visual and tactile differences, so that a mouse can tell the difference between sides. On the first day of testing, the time each mouse spends in either side of the apparatus is measured. For the next three days, the drug is "paired" with one side or the other by injecting the mouse (i.v. 2× the ED90 analgesic dose) and immediately confining it to that side. On the final day, the amount of time the mouse spends in the drug-paired side is determined and the percent change is calculated. If the percent change is positive, the drug is thought to be rewarding and likely to be abused by humans. Compounds demonstrating a lowered reinforcing effect than morphine will have reduced potential for causing addiction. Mice were tested for CPP as previously described (Lenard, N. R. et al. (2007) Eur. J. Pharmacol. 22, 560-564) and the procedure is briefly described below.

CPP Apparatus. The CPP apparatus is a plastic box, approximately 12 inches×6 inches×6 inches (l/w/h). One half of the box is transparent with a scored or textured floor and the other half of the box had blue vertical stripes with a smooth floor. The box is divided such that the mice can go from one side to the other through an opening or be confined to one side.

Conditioning. On day 1, each mouse is given two sets of IV injections. First, the mice are injected with saline and randomly confined to one side of the box for 30 minutes. The mice are then injected with the drug of interest (or saline, for control mice) and confined to the other side of the box ("drug-paired side") for 30 minutes. Doses of morphine and naloxone are used as previously described (Lenard, N. R. et al. (2007) Eur. J. Pharmacol. 22, 560-564). This conditioning paradigm is repeated for a total of three days.

Postconditioning. On day 4, the amount of time the mouse spends in each side of the box is recorded. Percent change in time spent in the drug-paired side is determined using the students t-test.

Figure 6:
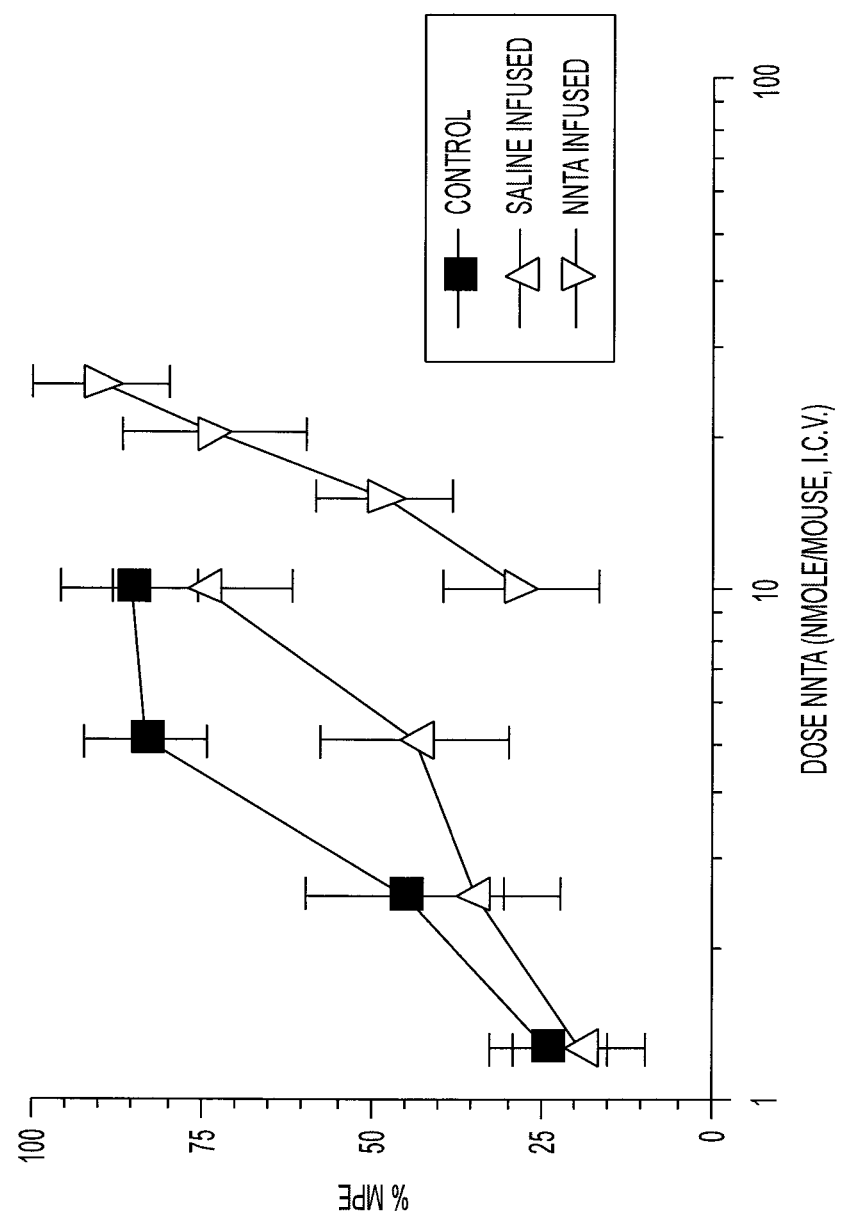
FIG. 6. Graded dose response curves for chronic i.c.v. administration of NNTA or saline. Percent maximum possible effect (% MPE) calculated from mouse tail flick data.
Figure 7:
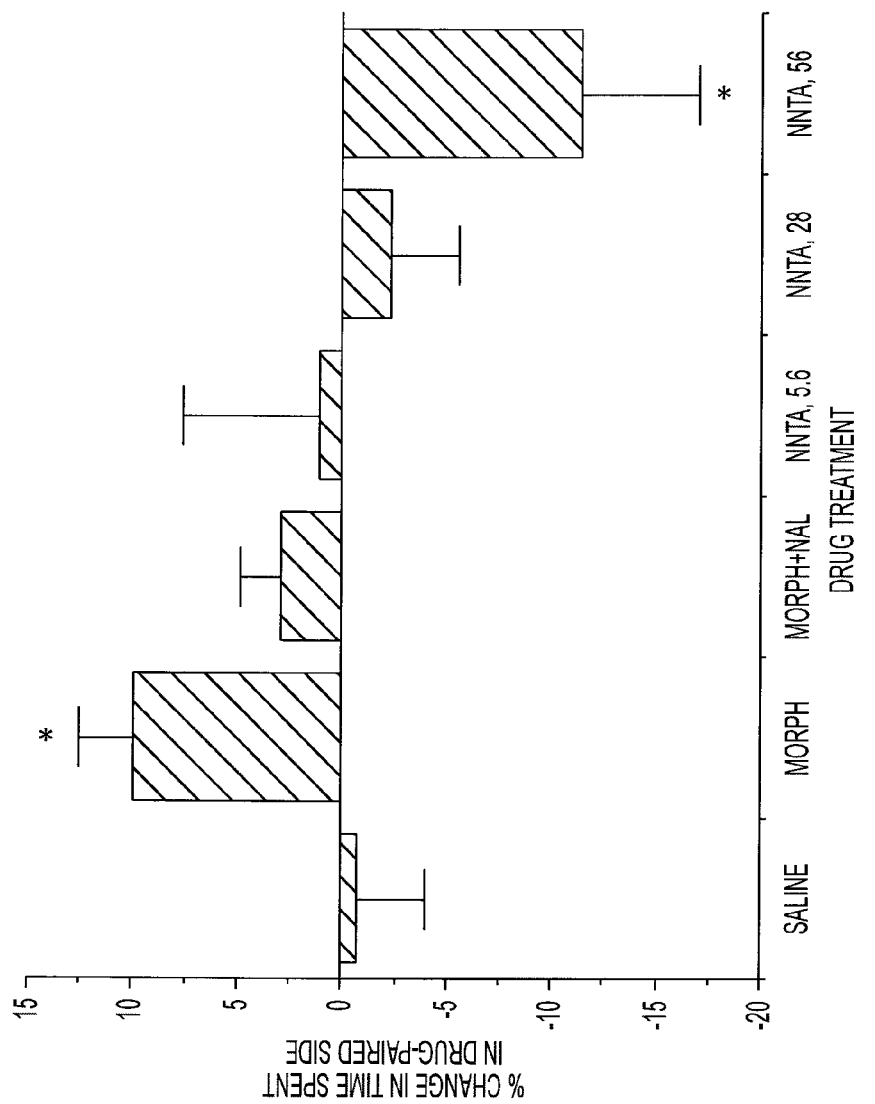
FIG. 7. Percent change in time spent in the drug paired side of a conditioned place preference apparatus in response to saline, morphine, morphine and naloxone, 5.6 nmol NNTA, 28 nmol NNTA or 56 nmol NNTA.

The tolerance and dependence experiments were performed using the compound of formula (I) and it was shown that NNTA produces little tolerance and no physical dependence (FIGS. 6 and 7).

The development of physical dependence was assessed by administering NNTA chronically i.c.v. for three days, followed by quantification of withdrawal jumping observed during precipitated withdrawal on the fourth day. Naloxone did not induce significant jumping in either saline (1.57±0.7 jumps) or NNTA (1.0±0.7 jumps) infused mice, indicating chronic NNTA does not produce physical dependence. In contrast, previous studies report naloxone induced 100 jumps in 10 min in i.c.v. morphine-infused mice, while the saline-infused mice jumped about 5 times in 10 min. The subsequent tail flick test indicated that NNTA produced some tolerance when administered chronically i.c.v. (FIG. 6), although it was substantially less robust when compared to morphine. Dose response curves obtained in the tail flick test for NNTA administered i.c.v. to naïve control mice, mice infused i.c.v. with saline and mice infused i.c.v. with NNTA are shown in FIG. 6. The $ED_{50}$ values calculated from these curves are: control, 2.5 (1.8-3.6); saline infused, 4.8 (2.8-8.1); and NNTA infused, 14.1 (11.9-17.5) nmol. These results indicate that a 3-fold tolerance developed to NNTA-induced antinociception. Previous studies using morphine in the same protocol showed a 6-fold development of tolerance to i.c.v. morphine. Thus, 3-fold tolerance but no physical dependence was produced after chronic i.c.v NNTA treatment, in contrast to 6-fold tolerance and robust physical dependence that develop after chronic i.c.v. morphine infusion.

Drug seeking behavior was investigated with conditioned place preference (CPP) studies, which indicated an absence of reward learning from the administration of NNTA (FIG. 7). There was a dose-related trend for aversion when a dose of NNTA was employed that produced 100% antinociception, but at the $ED_{50}$ dose no significant aversion was observed. Specifically, the two lower doses of NNTA (5.6 and 28 nmol) did not produce a significant effect on the time that the mice spent in the drug-paired chamber. However, NNTA produced a significant place aversion effect (p<0.1) at the 56 nmol dose, which had produced 100% antinociception in the tail flick test. As shown previously, morphine (1200 nmol/kg) produced a strong place preference, which can be blocked by naloxone (300 nmol/kg). The aversion of NNTA at a high dose is of interest because members of the clinically employed mixed agonist-antagonist class of opioids are known to produce dysphoria in humans.

The effects of a compound of the invention on GI transit can be determined using pharmacological models which are well known to the art, or using Test E described below.

Test E: Analgesia without Inhibition of GI Transit

GI Transit Assay

One unwanted side effect of treatment with opioids is constipation caused by opioid-induced inhibition of GI transit. To assay inhibition of the GI transit, drugs are administered IV via the tail vein in a volume of 100 µl to male ICR mice. Fifteen minutes later, antinociception is measured by the tail flick assay and a charcoal meal (300 µl, oral) is administered by gavage. Thirty minutes after the charcoal meal, the mice are sacrificed by halothane overdose and the distance the charcoal traveled relative to the entire length of the GI tract is compared to the distance traveled in control animals injected with saline.

In total, these data demonstrate that compounds of the invention are useful as analgesics. Specifically, the absence of physical dependence in mice, the small degree of antinociceptive tolerance upon chronic i.c.v administration and the lack of significant conditioned place preference at its $ED_{50}$ dose suggest that compounds of the invention do not have the undesirable side effects associated with morphine. Additionally, compounds of the invention may be useful as pharmacological tools for the further investigation of mu/kappa receptor function in vivo and in vitro.

The invention will now be illustrated by the following non-limiting Examples.

Melting points were determined on a Thomas-Hoover melting point apparatus and are uncorrected. $^1$H NMR spectra and $^{13}$C NMR spectra were taken on a Bruker 400 MHz instruments and calibrated using an internal reference. ESI mode mass spectra were recorded on a BrukerBioTOF II mass spectrometer. Elemental analyses were performed by M-H-W Laboratories, Phoenix, Ariz.

EXAMPLE 1

Preparation of the Compound of Formula (I)—NNTA

2-Naphthoic acid (1.1 mmol, 1.1 eq), 1-hydroxybenzotriazole (1.1 mmol, 1.1 eq), and b-naltrexamine (1.0 mmol, 1 eq) were dissolved in anhydrous DMF. The solution was cooled to 0° C. at which time dicyclohexylcarbodiimide (1.2 mmol, 1.2 eq) was added. The solution was sealed under a nitrogen atmosphere and stirred at room temperature overnight (16 hrs). TLC indicated the formation of two products (n-acylated and both n- and o-acylated). The reaction mixture was filtered (to remove DCU) into water (10× initial volume of DMF) and extracted with ethyl acetate (4 times). The organic layers were combined, dried over sodium sulfate, filtered and concentrated under reduced pressure to a white foam. This was taken up in methanol and potassium carbonate (5.0 mmol, 5 eq) was added and the suspension was stirred for 1 hour at room temperature. The mixture was then concentrated under reduced pressure and the residue was dissolved in water and extracted with ethyl acetate, dried over sodium sulfate, filtered and concentrated to yield 0.32 g of desired product which was subsequently converted into the HCl salt for biological testing. Melting points were determined on a Thomas-Hoover melting point apparatus and are uncorrected. $^1$H NMR spectra and $^{13}$C NMR spectra were taken on either a Varian Inova 300 MHz or Varian Unity 300 MHz instruments.
$^1$H NMR (DMSO-$d_6$): δ 0.01 (m, 2H); 0.35 (m, 2H); 0.74 (m, 1H); 1.33 (m, 4H); 1.82 (m, 2H); 2.07 (m, 1H); 2.23 (m, 1H); 2.41 (m, 1H); 2.89 (m, 2H); 3.04 (m, 1H); 3.64 (m, 1H); 4.67 (d, 1H, H-5, J=7.8 Hz); 4.81 (bs, 1H, OH-14, exc $D_2O$); 6.43 (d, 1H, H-2, J=8.1 Hz); 6.48 (d, 1H, H-$\overline{1}$, j=7.8 Hz); 7.50 (m, 2H, Ar); 7.89 (m, 4H, Ar); 8.39 (s, 1H, Ar); 8.71 (d, 1H, amide, J=7.5 Hz); 8.94 (bs, 1H, OH-3, exc $D_2O$); mp>250° C. Anal. calcd for $C_{36}H_{35}N_5O_5$: C, 69.84; H, 6.24; N, 5.26. Found: C, 66.81; H, 6.43; N, 4.98.

EXAMPLE 2

Alternate Preparation of the Compound of Formula (I)—NNTA (17-Cyclopropylmethyl-3,14β-dihydroxy-4,5α-epoxy-6β-[(2'naphthyl)acetamido]morphinan)

b-Naltrexamine (400 mg, 1.16 mmol), naphthoic acid (399 mg, 2.32 mmol) and BOP (1.03 g, 2.32 mmol) were dissolved in DCM (15 mL). To this solution, DIPEA (600 mL, 3.25 mmol) was added and the mixture was stirred at room temperature for 16 hours. The solution was concentrated under reduced pressure and the residue was taken up in MeOH (15 mL), and $K_2CO_3$ was added (1.2 g). After 1 hour at room temperature, the mixture was concentrated to dryness. The final crude was purified by $SiO_2$ chromatography (eluted with EtOAc/Hexanes: 4/1) to afford the desired compound as a white solid. The target compound was recrystallized from an acetone/hexanes (1/4: v/v) mixture providing a white solid (473 mg, 82%). The title compound was then subsequently converted into the HCl salt for biological testing.
Base Form of Compound of Formula (I)-NNTA
$^1$H NMR (DMSO-$d_6$) δ: 0.12 (m, 2H); 0.47 (m, 2H); 0.86 (m, 1H); 1.27-1.63 (m, 4H); 1.85-2.03 (m, 2H); 2.09 (m, 1H); 2.22 (m, 2H); 2.37 (m, 2H); 3.01 (m, 2H); 3.75 (m, 1H); 4.76 (d, 1H, $J_{H5-H6}$=7.8 Hz); 4.92 (bs, 1H, OH-14); 6.54 (d, 1H, $J_{H1-H2}$=8.1 Hz); 6.60 (d, 1H, $J_{H2-H1}$=8.1 Hz); 7.59-7.62 (m, 2H); 7.96-8.03 (m, 4H); 8.50 (s, 1H), 8.84 (d, 1H amide, $J_{NH-H6}$=8.2 Hz); 9.05 (bs, 1H, OH-3); $^{13}$C NMR (DMSO-$d_6$) δ: 3.52, 3.65, 9.21, 22.12, 24.69, 30.06, 30.27, 43.66, 47.01, 51.63, 58.35, 61.71, 69.58, 90.64, 116.93, 118.36, 123.45, 124.08, 126.68, 127.43, 127.55 (×2), 127.77, 128.80, 131.36, 131.58, 132.08, 134.05, 140.41, 142.06, 165.52; mp=199-201° C. Anal. Calcd. for $C_{31}H_{32}N_2O_4$: C, 74.98; H, 6.50; N, 5.64. Found: C, 73.85; H, 6.13; N, 5.52. ESI-TOF MS m/z: 497.2930 (MH$^+$), 993.5777 (2×MH$^+$)
Salt Form of Compound of Formula (I)—NNTA
$^1$H NMR salt form (DMSO-$d_6$) δ: 0.53-0.68 (m, 4H); 1.08 (m, 1H); 1.46 (m, 2H); 1.63 (m, 1H); 1.79-1.95 (m, 2H); 2.48 (m, 2H); 2.87 (m, 2H); 3.03-3.12 (m, 2H); 3.35 (m, 2H); 3.75 (m, 1H); 3.90 (m, 1H); 4.90 (d, 1H, $J_{H5-H6}$=7.8 Hz); 6.29 (bs, 1H, OH-14); 6.65 (d, 1H, $J_{H1-H2}$=8.1 Hz); 6.74 (d, 1H, $J_{H2-H1}$=8.1 Hz); 7.59-7.62 (m, 2H); 7.97-8.03 (m, 4H); 8.52 (s, 1H), 8.90 (d, 1H amide, $J_{NH-H6}$=8.2 Hz); 9.38 (bs, 1H, O H-3); $^{13}$C NMR salt form (DMSO-$d_6$) δ: 2.57, 5.10, 5.70, 22.99, 23.80, 27.30, 29.32, 40.07, 45.56, 46.45, 51.23, 56.59, 61.56, 69.69, 89.86, 117.83, 119.23, 120.59, 124.05, 126.71, 127.49, 127.57 (×2), 127.81, 128.80, 129.66, 131.44, 132.07, 134.09, 141.28, 142.10, 165.59 mp>260° C. Anal. Calcd. for $C_{31}H_{33}ClN_2O_4$: C, 69.85; H, 6.24; N, 4.67. Found: C, 67.79; H, 6.44; N, 4.67. ESI-TOF MS m/z: 497.2930 (MH$^+$)

EXAMPLE 3

The following illustrate representative pharmaceutical dosage forms, containing a compound of formula (I) or a pharmaceutically acceptable salt thereof ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

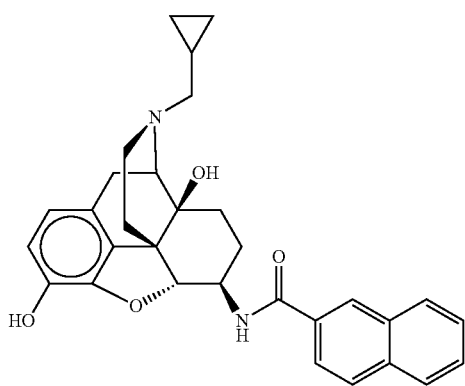

(I)

or a salt thereof.

2. The compound of claim 1 which is a compound of formula (I) or a pharmaceutically acceptable salt thereof.

3. A pharmaceutical composition comprising a compound of formula (I) as described in claim 1, or a pharmaceutically acceptable salt thereof; and a pharmaceutically acceptable diluent or carrier.

4. A method for producing analgesia in an animal comprising administering a compound of formula (I) as described in claim 1, or a pharmaceutically acceptable salt thereof, to the animal.

5. A method for producing analgesia in an animal, comprising administering to the animal an amount of a compound of formula (I) as described in claim 1, or a pharmaceutically acceptable salt thereof, that is effective to produce analgesia while causing less inhibition of GI transit than is caused by administration of a similar effective dosage of morphine to the animal.

6. A method for producing analgesia in an animal, comprising administering to the animal an amount of a compound of formula (I) as described in claim 1, or a pharmaceutically acceptable salt thereof, that is effective to produce analgesia while causing less dependence than is caused by administration of a similar effective dosage of morphine to the animal.

7. A method for producing analgesia in an animal, comprising administering to the animal an amount of a compound of formula (I) as described in claim 1, or a pharmaceutically acceptable salt thereof, that is effective to produce analgesia while causing less tolerance than is caused by administration of a similar effective dosage of morphine to the animal.

8. The method of claim 4, wherein the animal is a human.

* * * * *

UNITED STATES PATENT AND TRADEMARK OFFICE
CERTIFICATE OF CORRECTION

PATENT NO. : 8,609,682 B2  
APPLICATION NO. : 13/003691  
DATED : December 17, 2013  
INVENTOR(S) : Portoghese et al.

Page 1 of 1

It is certified that error appears in the above-identified patent and that said Letters Patent is hereby corrected as shown below:

In the Specification

On page 1, column 1, at line 11, please replace the below paragraph;

Government Funding

The invention described herein was made with Government support under Grant Number DA01533 awarded by NIDA. The United States Government has certain rights in the invention.

With the following revised paragraph:

Government Funding

This invention was made with government support under DA001533 awarded by the National Institutes of Health. The government has certain rights in the invention.

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,609,682 B2  Page 1 of 1
APPLICATION NO. : 13/003691
DATED : December 17, 2013
INVENTOR(S) : Portoghese et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Twenty-second Day of September, 2015

Michelle K. Lee
*Director of the United States Patent and Trademark Office*